United States Patent
Okamura

(12) 
(10) Patent No.: US 9,089,335 B2
(45) Date of Patent: Jul. 28, 2015

(54) INTRODUCER SHEATH ASSEMBLY AND METHOD

(71) Applicant: Ryo Okamura, Shizuoka (JP)

(72) Inventor: Ryo Okamura, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 218 days.

(21) Appl. No.: 13/629,264

(22) Filed: Sep. 27, 2012

(65) Prior Publication Data

US 2013/0023734 A1    Jan. 24, 2013

Related U.S. Application Data

(63) Continuation of application No. PCT/JP2011/057427, filed on Mar. 25, 2011.

(30) Foreign Application Priority Data

Mar. 29, 2010    (JP) .................................. 2010-074563

(51) Int. Cl.
*A61B 17/132* (2006.01)
*A61B 17/135* (2006.01)
*A61M 25/00* (2006.01)
*A61M 25/02* (2006.01)
(Continued)

(52) U.S. Cl.
CPC ............ *A61B 17/1325* (2013.01); *A61B 17/135* (2013.01); *A61M 25/0097* (2013.01); *A61M 25/02* (2013.01); *A61M 29/00* (2013.01); *A61M 25/0662* (2013.01); *A61M 2025/0206* (2013.01); *A61M 2025/026* (2013.01); *A61M 2025/0213* (2013.01); *A61M 2025/0266* (2013.01)

(58) Field of Classification Search
CPC ................................................... A61B 17/1325
USPC .......................................................... 606/201
See application file for complete search history.

(56) References Cited

U.S. PATENT DOCUMENTS 3,675,656 A * 7/1972 Hakim ........................... 606/158
4,314,568 A * 2/1982 Loving ........................... 606/201
(Continued)

FOREIGN PATENT DOCUMENTS

CN        2429120 Y     5/2001
CN     201220032 Y     4/2009
(Continued)

OTHER PUBLICATIONS

International Search Report from the International Bureau of WIPO for International Application No. PCT/JP2011/057427 dated Apr. 26, 2011 (1 page) and an English translation of the same (1 page).
(Continued)

*Primary Examiner* — David Bates
(74) *Attorney, Agent, or Firm* — Fitch Even Tabin & Flannery LLP

(57) ABSTRACT

An introducer sheath assembly is provided that is capable of securely fastening a sheath tube to a patient's limb so as to keep it from being displaced after insertion into an incision. The introducer sheath assembly has an introducer sheath including a sheath tube to be inserted into the incision made on the patient's limb and a sheath hub attached to the proximal end of the sheath tube. In one form, the introducer sheath assembly has a belt, which is connected to the sheath hub and wound around the limb, and a fastening member to fasten the belt wound around the limb.

12 Claims, 7 Drawing Sheets

(51) Int. Cl.
*A61M 29/00* (2006.01)
*A61M 25/06* (2006.01)

(56) References Cited

U.S. PATENT DOCUMENTS

| | | | | |
|---|---|---|---|---|
| 5,269,803 A * | 12/1993 | Geary et al. | ................... | 606/201 |
| 5,307,811 A * | 5/1994 | Sigwart et al. | ................. | 600/490 |
| 5,433,724 A * | 7/1995 | Kawasaki et al. | .............. | 606/202 |
| 5,464,420 A * | 11/1995 | Hori et al. | ..................... | 606/202 |
| 5,486,194 A * | 1/1996 | Kawasaki et al. | .............. | 606/203 |
| 5,690,610 A * | 11/1997 | Ito et al. | .......................... | 602/53 |
| 5,968,072 A * | 10/1999 | Hite et al. | ...................... | 606/202 |
| 7,927,295 B2 * | 4/2011 | Bates et al. | ..................... | 602/13 |
| 8,353,927 B2 * | 1/2013 | Lampropoulos et al. | ..... | 606/204 |
| 2004/0098035 A1 | 5/2004 | Wada et al. | | |
| 2007/0239092 A1* | 10/2007 | Ross | ............................... | 602/20 |
| 2009/0281565 A1* | 11/2009 | McNeese | ..................... | 606/201 |

FOREIGN PATENT DOCUMENTS

| | | |
|---|---|---|
| EP | 0 655 258 A1 | 5/1995 |
| EP | 1 382 306 A2 | 1/2004 |
| JP | H11-206888 A | 8/1999 |
| JP | 2004-154413 A | 6/2004 |
| JP | 2009-507597 A | 2/2009 |
| JP | 2009-537210 A | 10/2009 |
| WO | 2007/031707 A1 | 3/2007 |
| WO | 2007/132444 A2 | 11/2007 |

OTHER PUBLICATIONS

Office Action issued in corresponding Chinese Application No. 201180017027.6 dated Dec. 9, 2013 (6 pages).

Extended European Search Report and European Search Opinion issued in counterpart European Application No. 11 762 719.0, dated Aug. 13, 2013 (8 pages).

* cited by examiner

INTRODUCER SHEATH ASSEMBLY AND METHOD

CROSS-REFERENCE TO RELATED APPLICATIONS

This application is a continuation of International Application Number PCT/JP2011/057427, filed on Mar. 25, 2011, which claims priority from JP 2010-074563, filed on Mar. 29, 2010, which are hereby incorporated herein by reference in their entirety.

FIELD OF THE INVENTION

The invention relates to an introducer sheath assembly and, more particularly, to a hemostatic introducer sheath assembly and method of securing an introducer sheath assembly.

Recent medical treatments often employ a medical device called a catheter, which is a thin long hollow tubular body, for therapy and examination of various kinds. The catheter for that purpose achieves the direct administration of a drug to the lesion owing to its length, the expansion of a stenosis in the body cavity with the help of a balloon which is capable of expansion when pressurized attached to the distal end thereof, the opening of a lesion by shaving with the help of a cutter attached to the distal end thereof, or the closing of the aneurysm, bleeding part, and feeding vessel with a wadding carried thereby. Moreover, the catheter is also used for placement of a stent, which is a tubular body with a side wall of mesh structure and keeps a stenosis open in the body cavity. Another use of the catheter is for the suction of excess fluid from the body cavity.

Therapy and examination with a catheter usually requires a catheter introducer which includes an introducer sheath and a sheath tube attached thereto. With the sheath tube inserted into an incision formed on the arm or leg, the introducer sheath permits the catheter to be introduced through the skin to the lesion such as in a blood vessel by way of the lumen of the introducer sheath.

For skillful and precise manipulation of the catheter and guide wire, the sheath tube inserted into the incision should be protected against displacement. According to Patent Document 1: JP-T-2009-537210 (see paragraph 0045) this object is achieved by providing the catheter inserting device with adhesive-coated projections resembling wings which keep the tube inserted into the incision fixed on the patient's body. It also discloses that the projections may have holes through which is passed a band to fix the sheath tube to the patient's body.

SUMMARY OF INVENTION

Unfortunately, the projections with adhesive coating are not satisfactory for fixing the tube to the patient's body so that its protected against displacement. Thus, the prior method does not ensure the skillful manipulation of the catheter and guide wire. In addition, the method that utilizes a band passing through the holes made in the projections is complicated and thus requires significant work for fixing the wings on the patient's body.

The present invention was completed to address the foregoing problems involved in the prior art. Accordingly, it is one object of the present invention to provide an introducer sheath assembly which securely fixes the sheath tube without displacement from the incision into which the sheath tube has been inserted and which is easy to attach to the patient's limb.

In one form, the introducer sheath assembly, which has been developed to achieve the above-mentioned object, has an introducer sheath including a sheath tube to be inserted into the incision made on the patient's limb and a sheath hub attached to the proximal end of the sheath tube. Moreover, the introducer sheath assembly has a belt, which is connected to the sheath hub and wound around the limb, and a fastening member to fasten the belt wound around the limb.

The introducer sheath assembly according to one form of the present invention is used in such a way that the sheath hub is securely fastened to the patient's limb by the belt which is wound completely around the limb and hence the possibility of the sheath hub and sheath tube being displaced during operation is minimized. The fastening of the sheath in this way keeps the sheath tube which has been introduced into the blood vessel in position even though the sheath hub is accidentally touched or engaged during operation. This helps the operator to manipulate the catheter and guide wire more precisely and skillfully. Moreover, the belt connected to the sheath hub permits the operator to fasten the introducer sheath easily to the patient's limb.

In another form, an introducer sheath assembly is provided including an introducer sheath having an elongate body for insertion into an incision in a patient's limb. An elongate securing device is operatively connected to the elongate body to extend transversely thereto and is sized for extending about the patient's limb. A connector mechanism of the elongate securing device is operable to releasably secure the elongate securing device about the patient's limb to urge a portion of the introducer sheath elongate body that remains outside the patient's body into tight engagement with the patient's limb.

Preferably, the elongate securing device includes an elongate belt member, and the connector mechanism includes a hook-and-loop fastener having male and female portions thereof adjacent opposite ends of the elongate belt member that allow the elongate belt member to be tightly secured about the patient's limb to exert a downward pulling force on either side of the introducer sheath elongate body portion.

In yet another form, a hemostatic band device for an introducer sheath assembly is provided with the introducer sheath assembly having an introducer sheath including an elongate body having an enlarged, sheath hub portion and a tube portion for being inserted into an incision in a patient's limb. A hemostatic band is provided for being operatively connected to the sheath elongate body to extend transversely thereto and is sized to extend about the patient's limb. At least one balloon of the hemostatic band is expandable to apply pressure to an area of the patient's limb surrounding the incision. Introducer sheath receiving structure of the hemostatic band is configured for removably receiving the sheath hub portion with the tube portion extending beyond the introducer sheath receiving structure to be inserted in the incision.

In another aspect of the invention, a method of securing an introducer sheath assembly to a patient's limb is provided. The method includes aligning introducer sheath receiving structure attached to a belt of the introducer sheath assembly with an incision to be adjacent thereto; securing the belt to extend about the patient's limb; and placing an introducer sheath in the sheath receiving structure for extending into the adjacent incision with the secured belt resisting displacement of the introducer sheath when engaged during use thereof.

DETAILED DESCRIPTION OF THE PREFERRED EMBODIMENTS

Figure 1:
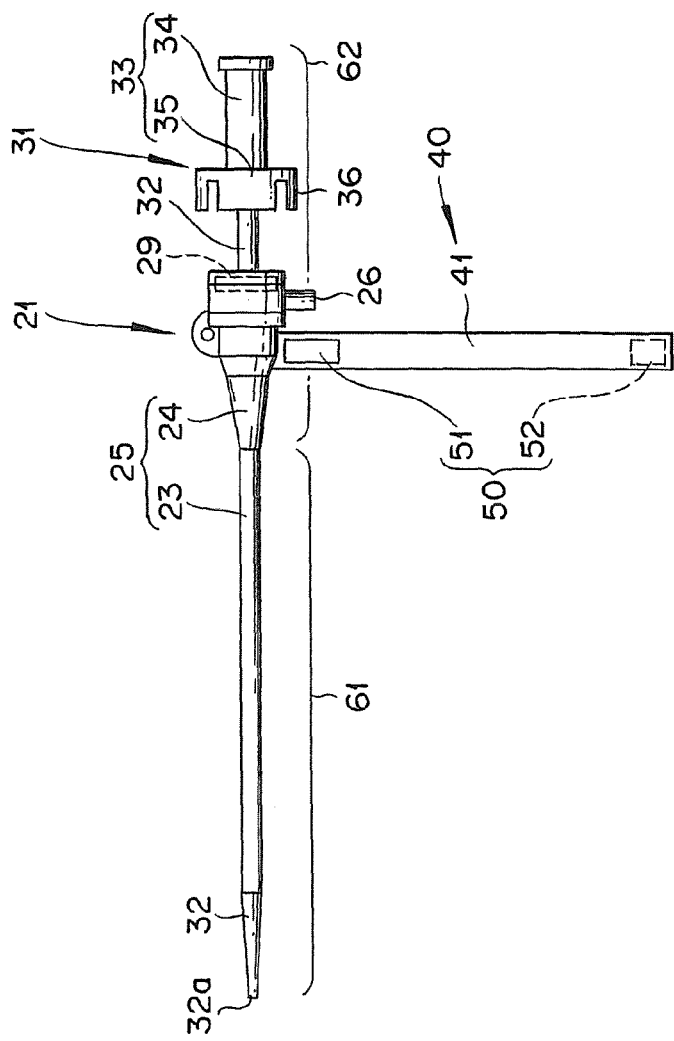
FIG. 1 is a front view depicting the catheter introducer pertaining to the first embodiment.

The embodiments of the present invention will be described below with reference to the accompanying drawings, in which identical elements are given identical symbols to avoid repeated descriptions. The dimensions in the drawings are exaggerated for the sake of easy illustration and are different from actual ones.

The catheter introducer 10 is a device that establishes the access route into a body cavity. Incidentally, generally the following description uses the term "proximal end" to denote that side of the device which is used for operation and the term "distal end" to denote that side of the device which is inserted into the body cavity.

Figure 2:
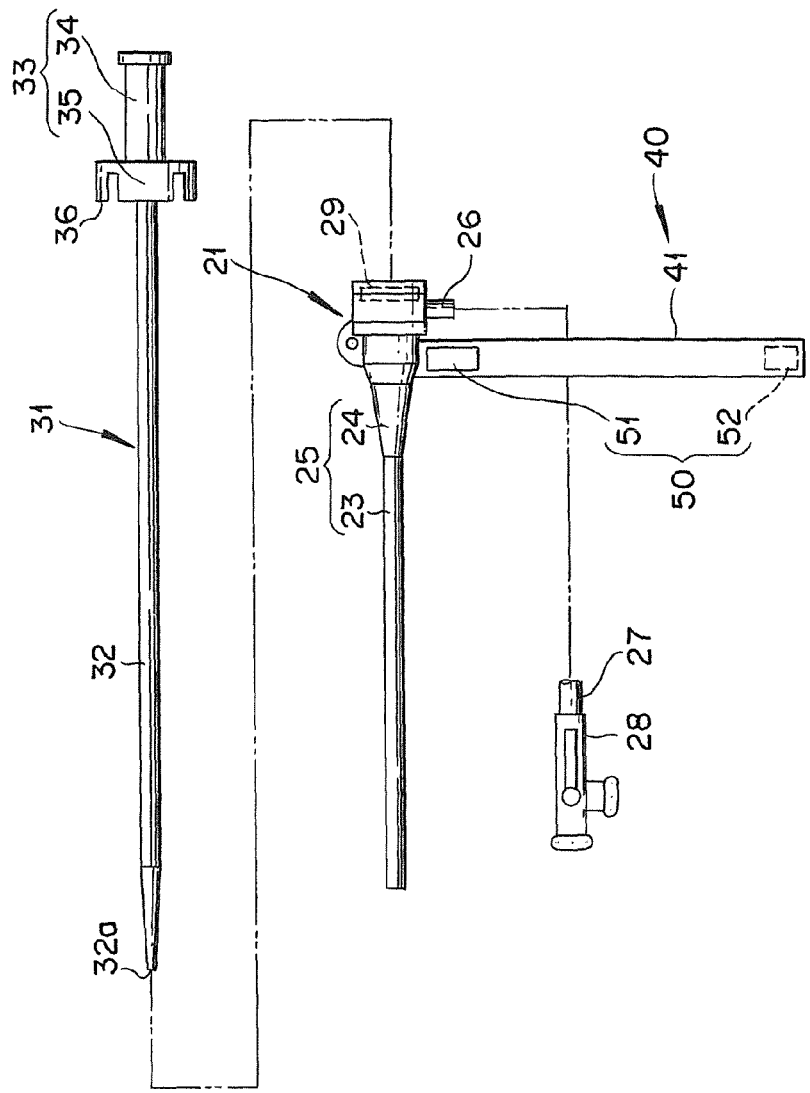
FIG. 2 is a plan view depicting the catheter introducer which has been separated into the introducer sheath assembly and the dilator.
Figure 3:
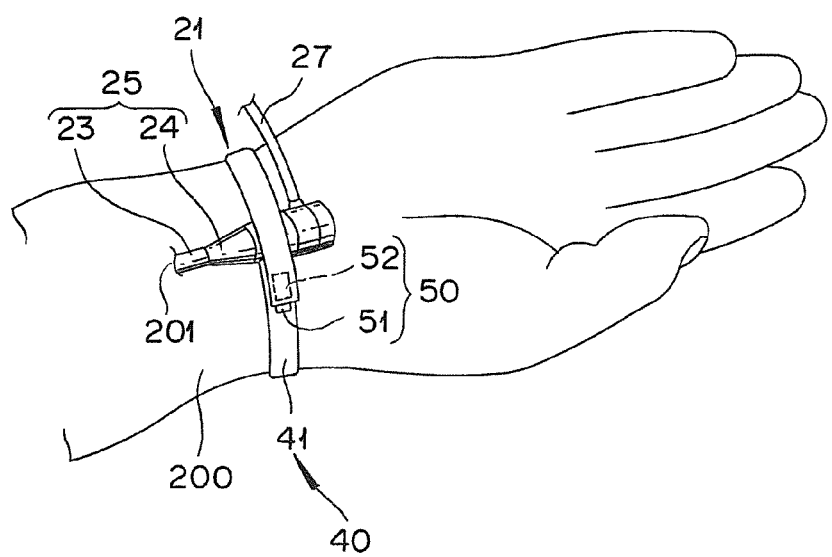
FIG. 3 is a diagram showing how the introducer sheath assembly pertaining to the first embodiment is mounted on the patient's wrist.

The catheter introducer 10 shown in FIGS. 1 and 2 is composed of the introducer sheath assembly 21 and the dilator 31. The introducer sheath assembly 21 is composed of the introducer sheath 25 having an elongate body including the sheath tube 23 to be inserted into the incision 201 made in the skin of the patient's limb 200 (as shown in FIG. 3) and the sheath hub 24 attached to the proximal end of the sheath tube 23. The introducer sheath assembly 21 further has an elongate securing device in the form of the belt 40 which is connected to the sheath hub 24 and is sized to be wound around and extend about the patient's limb 200 and a connector mechanism or fastening member 50 which keeps the belt 40 wound around the limb 200. The dilator 31 is composed of the dilator tube 32 and the dilator hub 33 attached to the proximal end of the dilator tube 32. The dilator tube 32 is passed through the sheath tube 23 so that it functions as a core when the sheath tube 23 is inserted into the incision 201. After the sheath tube 23 has been inserted into the incision 201, that part indicated by the reference numeral 61 in FIG. 1 which includes the sheath tube 23 and the dilator tube 32 resides under the skin and in a blood vessel. In addition, that part indicated by the reference numeral 62 which includes the sheath hub 24 and the dilator hub 33 remains outside the skin.

The introducer sheath 25 mentioned above is intended to facilitate insertion of the catheter, guide wire, wadding, etc. into the body cavity.

The sheath tube 23 is introduced into the body cavity through the skin. The sheath tube 23 is formed from any one or more as a mixture of polymeric materials including polyolefin (such as polyethylene, polypropylene, polybutene, ethylene-propylene copolymer, ethylene-vinyl acetate copolymer, ionomer, and a mixture of two or more thereof), polyolefin elastomer, cross-linked polyolefin, polyvinyl chloride, polyamide, polyamide elastomer, polyester, polyester elastomer, polyurethane, polyurethane elastomer, fluoroplastics, polycarbonate, polystyrene, polyacetal, polyimide, and polyetherimide.

The sheath hub 24 has the side port 26 for communication with the inside passageway of the sheath tube 23. The side port 26, shown in FIG. 2, is fluid-tightly joined to one end of the flexible tube 27 made of polyvinyl chloride or the like. The other end of the tube 27 is connected to the three-way stopcock 28, which permits infusion of a fluid like physiological saline from a port thereof into the introducer sheath 25 through the tube 27. At the proximal end of the sheath hub 24, a hemostatic valve 29 is provided which permits free passage of the dilator tube 32 and the catheter therethrough. The sheath hub 24 is formed from a hard plastic material or the like, such as polyolefin such as polyethylene and polypropylene, polyamide, polycarbonate, and polystyrene.

The dilator 31 mentioned above protects the sheath tube 23 against bending or expands the incision made on the skin when the introducer sheath 25 is inserted into the blood vessel or the like.

The dilator tube 32 is passed through the through passageway of the sheath tube 23, such that the tip 32a of the dilator tube 32 extends out from and beyond the distal tip of the sheath tube 23. The dilator tube 32 may be formed from the same material as the sheath tube 23.

The dilator hub 33 is composed of the dilator hub proper 34 and the flange 35 attached to the distal end of the dilator hub proper 34. The flange 35 has a plurality of arms 36 extending therefrom toward the distal end. The arms 36 are elastic such that they freely engage with and disengage from the proximal end of the sheath hub 24. The dilator hub 33 may be formed from the same material as the sheath hub 24.

According to the first embodiment, the belt 40 (mentioned above) is constructed of the belt member 41, with one end thereof connected to the sheath hub 24. The belt member 41 has a length that is more than sufficient to be wound around the limb 200 and the sheath hub 24.

The belt member 41 has a male part 51 (or a female part 52) of the hook-and-loop fastener 50 which is the one generally called MagicTape (registered trademark) adjacent one end of the belt member 41 on the front side thereof (front side of the paper of FIG. 1). The belt member 41 also has the female part 52 (or the male part 51) of the hook-and-loop fastener 50 adjacent the other end of the belt member 41 on the rear side thereof (rear side of the paper of FIG. 1). The hook-and-loop fastener 50 functions as a fastening member.

Operation of the first embodiment will be explained below.

The procedure to insert the introducer sheath 25 into the artery in the wrist 200 (as a limb) includes the following steps. First, the dilator tube 32 is passed through the sheath tube 23. Next, the arms 36 of the dilator hub 33 are engaged with the sheath hub 24, so that the introducer sheath 25 and the dilator 31 are firmly combined and connected together.

The sheath tube 23 is inserted into the incision 201. The belt member 41 is wound around the wrist 200 and the sheath hub 24 and fastened by means of the male part 51 and female part 52 of the hook-and-loop fastener 50. With this insertion step completed, the sheath tube 23 and the dilator tube 32 stay in the blood vessel and the sheath hub 24 and dilator hub 33 remain outside the skin.

After the introducer sheath 25 has been inserted and fastened by the belt member 41, the dilator hub 33 has its arms 36 disengaged from the sheath hub 24 and the dilator 31 is withdrawn, with the introducer sheath 25 remaining in place, as shown in FIG. 3. In this state, the introducer sheath 25 functions as a passage between the blood vessel and the outside, and it permits the catheter or the like to be inserted into the blood vessel.

During the course of the procedures mentioned above, the sheath hub 24 remains outside the patient's body and the dilator hub 33 also remains outside the patient's body until the dilator 31 is withdrawn. Being fastened to the wrist 200 by the belt member 41 wound around the wrist 200, the sheath hub 24 is less liable to displacement and hence the sheath tube 23 is also less liable to displacement.

The belt member 41, which is entirely wound around the wrist 200, urges and pushes or pulls the sheath hub 24 wholly against the wrist 200 with a strong fastening force thereby fixing the sheath hub 24 more strongly.

Thus, the sheath tube 23, which has been inserted into the blood vessel, is securely fastened to such an extent that it will not be displaced even though the sheath hub 24 or the dilator hub 33 is touched or engaged by the operator. This facilitates the accurate and precise manipulation of the catheter and guide wire. Moreover, the fact that the belt member 41 is connected to the sheath hub 24 also facilitates the step of attaching the introducer sheath 25 to the wrist 200.

The embodiment mentioned above demonstrates the mode in which the belt member 41 is wound around the wrist 200 as well as the sheath hub 24. However, it is not necessary to wind the belt member around the sheath hub if the belt member and the sheath hub are fastened to each other. It is possible to fasten the belt member to the sheath hub by providing the sheath hub with wing-like flanges extending in both directions of the sheath hub with the flanges placed against the limb, with one of the flanges fixed to one end of the belt member and the other one of the flanges fixed to the other end of the belt member by means of a hook-and-loop fastener.

The belt 40 is not restricted in structure to the belt member 41 described above, but it may be variously modified according to need. According to the second embodiment shown in FIGS. 4 to 6, a hemostatic band device is illustrated and the belt 40 thereof is in the form of a hemostatic band 42 which is so configured to stop bleeding by operation of the balloon 72 which is capable of expanding by being filled with a fluid, thereby pressing against the incision 201 to apply pressure thereto. This hemostatic band 42 is intended to stop bleeding from the incision 201 made in the skin of the wrist 200 after the introducer sheath 25 used for insertion of the catheter or the like into the blood vessel for therapy and examination has been withdrawn. The second embodiment will be described below with reference to FIGS. 4 to 6, in which those elements common to the first embodiment are given identical symbols to partly avoid repeated descriptions.

According to the second embodiment, the introducer sheath assembly 22 is composed of the introducer sheath 25, the hemostatic band 42 as the band 40 which is connected to the sheath hub 24 and wound around the limb 200, and the hook-and-loop fastener 50 which fastens the hemostatic band 42 wound around the limb 200.

The hemostatic band 42 includes the main band portion or band proper 71, a pressing device which, in one form, includes the balloon 72 that expands upon introduction of a fluid thereinto, and the auxiliary balloon 73 that is aligned or overlaps with the balloon 72. The hemostatic band 42 additionally has a receiving portion or introducer sheath receiving structure in the form of holding part 80 which detachably holds the introducer sheath 25. The holding part 80 includes the pocket 81 which accommodates and holds the sheath hub 24 and the window 82 which opens through the pocket 81 and permits the sheath tube 23 to pass therethrough. The window 82 is so arranged as to be adjacent the position (incision 201) at which bleeding is to be stopped by the balloon 72. According to the illustrated embodiment, the window 82 lies on the extension of the line passing through the position that requires the stopping of bleeding and the pocket 81 so as to be aligned with the incision 201. The arrangement of the window 82 in this manner makes it possible to insert the sheath tube 23 at a desirable position of the wrist 200, without the pocket 81 interfering with the sheath tube 23 when the hemostatic band 42 is wound around the wrist 200 (See FIG. 5).

The band proper 71 is a flexible belt-like member. It is wound around the wrist 200 and the sheath hub 24, with both ends thereof overlapping with each other. The band proper 71 is made of any translucent material for the incision 201 to be visible. Examples of such materials include polyvinyl chloride, polyolefins such as polyethylene, polypropylene, polybutadiene, and ethylene-vinyl acetate copolymer (EVA), polyesters such as polyethylene terephthalate (PET), and polybutylene terephthalate (PBT), thermoplastic elastomers such as polyvinylidene chloride, silicone, polyurethane, polyamide elastomer, polyurethane elastomer, and polyester elastomer, and a combination thereof (in the form of resin blend, polymer alloy, laminate, and the like). It is desirable that the band proper 71 is substantially transparent, so that the operator can see the incision 201 and can accurately position the band proper 71 for use of the hemostatic band 42 to stop bleeding from the incision 201 as described hereinafter. For the same reason as above, it is also desirable to use a substantially transparent material for the balloon 72, the auxiliary balloon 73, the pocket 81, and the bent plate 74 also to be described hereinafter.

The band proper 71 has at the center thereof the bent plate holding part 75 to hold the bent plate 74. The bent plate holding part 75 has a gap thereto in which the bent plate 74 is held. The band proper 71 holds the bent plate 74 in such a way that the bent plate 74, the balloon 72 and the auxiliary balloon 73 overlap with one another. The bent plate 74 is made of a material which is stiffer than that used for the band proper 71, so that it maintains its shape.

Figure 4:
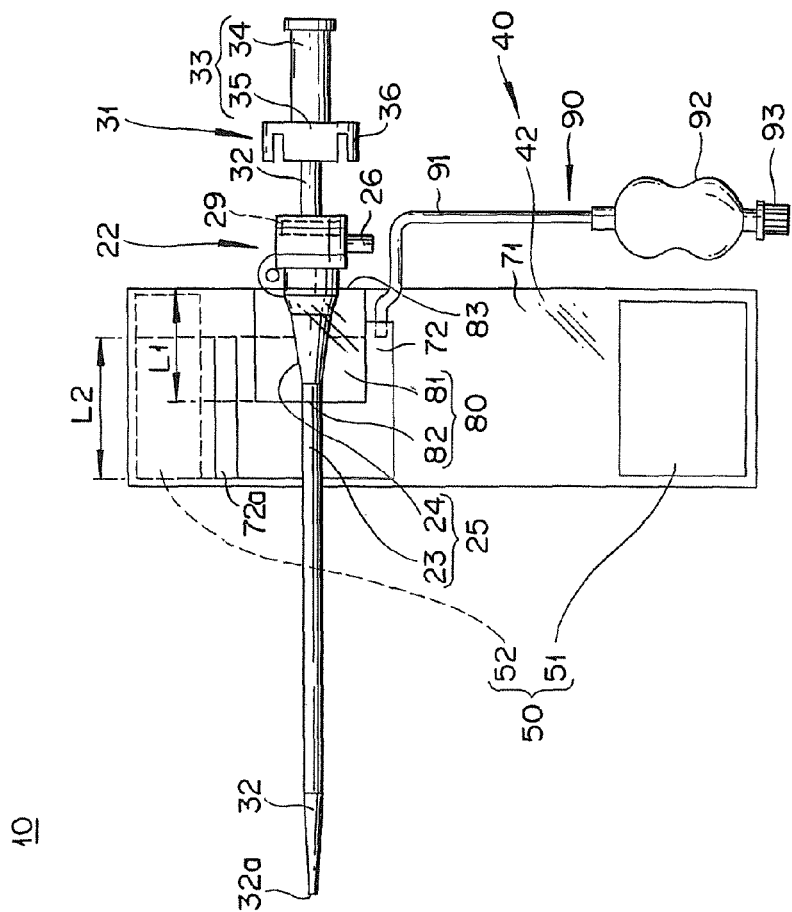
FIG. 4 is a front view depicting the catheter introducer pertaining to the second embodiment.

The band proper 71 shown in FIG. 4 has the male part 51 (or the female part 52) of the hook-and-loop fastener 50 on the inside (or the front side of the paper of FIG. 4) near the lower end thereof. Also, the band proper 71 shown in FIG. 4 has the female part 52 (or the male part 51) of the hook-and-loop fastener 50 on the outside (or the back side of the paper of FIG. 4) near the upper end thereof. With the male and female parts 51 and 52 of the hook-and-loop fastener 50 joined together, the band proper 71 is fixed after it has been wound around the wrist 200 and the sheath hub 24.

Figure 6:
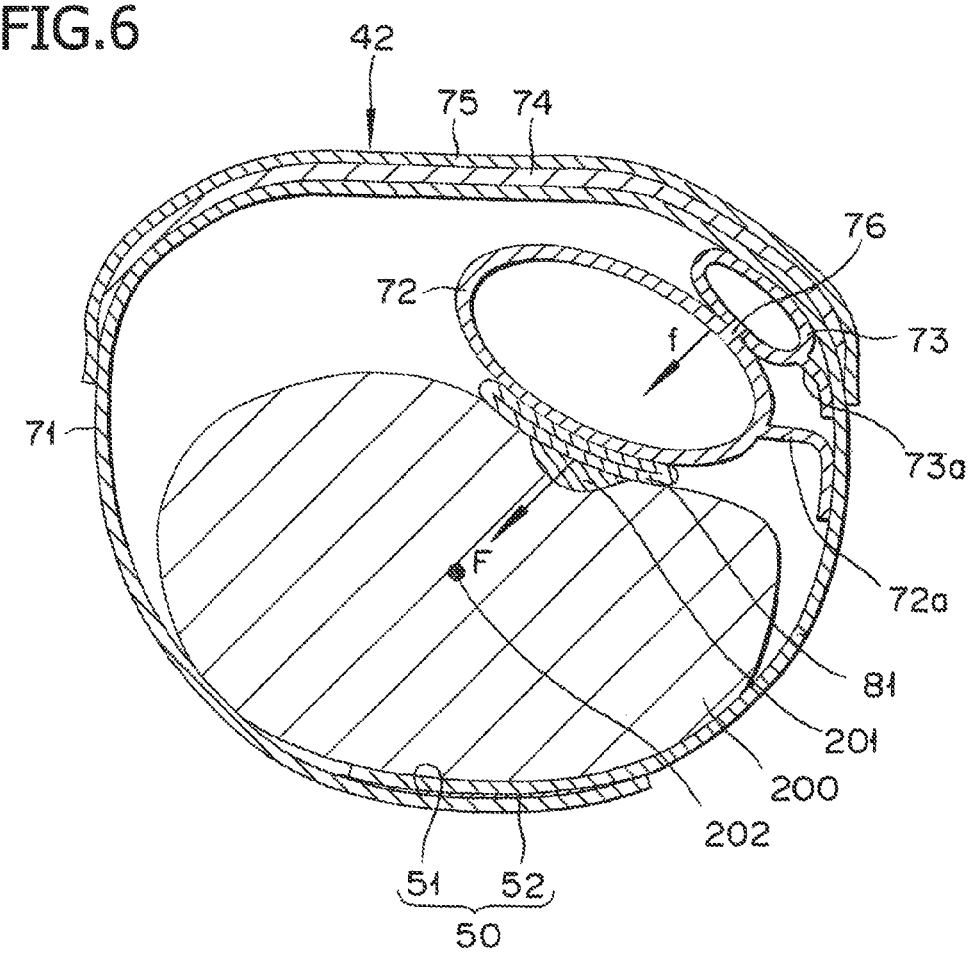
FIG. 6 is a sectional view showing how to stop bleeding by pressing the incision with the hemostatic band.

The balloon 72 and the auxiliary balloon 73 are made of any flexible material, so that they expand upon injection of a fluid (liquid or gas such as air) therein. The balloon 72 takes on a square shape when it is collapsed. The material for the balloon 72 and the auxiliary balloon 73 is not specifically restricted so long as it makes the incision 201 visible. This material may be the same as set forth above which is used for the band proper 71. As shown in FIG. 6, the balloon 72 is joined to the band proper 71 through the joining member 72a, and the auxiliary balloon 73 is joined to the band proper 71 through the joining member 73a. A portion of the balloon 72 and a portion of the auxiliary balloon 73 are joined to each other. In the joining part, communicating member 76 is formed for communication between the inside of the balloon 72 and the inside of the auxiliary balloon 73. The communicating member 76 permits the fluid, which has been injected into the balloon 72, to partly flow into the auxiliary balloon 73, so that the auxiliary balloon 73 expands as the balloon 72 expands. In this way it is possible to expand both of them by a single operation, which leads to efficient operation.

The auxiliary balloon 73 is smaller in size than the balloon 72, so that the auxiliary balloon 73 locally presses the balloon 72. The direction of pressing is indicated by the arrow f in FIG. 6, which is directed toward the approximate center 202 of the wrist 200. The pressing force of the auxiliary balloon 73 causes the balloon 72 to apply a pressing force to the incision 201 in the direction indicated by the arrow F in FIG. 6. The direction of pressing (stressing) is not vertical (perpendicular to the surface of the wrist 200) but aslant (toward the center 202 of the wrist 200). Pressing in this manner is more effective for hemostatic action than pressing (stressing) the incision 201 in the vertical direction.

The balloon 72 has the injecting member 90 connected thereto, so that the balloon 72 can be filled with a fluid injected from the injecting member 90, as shown in FIG. 4. The injecting member 90 is composed of the flexible tube 91 whose distal end connects with the balloon 72 and whose lumen communicates with the inside of the balloon 72, the bag 92 attached to the proximal end of the tube 91, and the tubular connector 93 attached to the bag 92. The balloon 72 is expanded (inflated) as the operator pushes the plunger of the syringe (not shown), whose distal tip end is inserted into the connector 93, to inject a fluid into the balloon 72 through the injecting member 90. After injection of a fluid into the balloon 72, the distal tip end of the syringe is withdrawn from the connector 93. The balloon 72 remains expanded because the connector 93 has a check valve which closes to prevent the back flow of fluid.

The pocket 81 is a bag-like object which receives and holds the sheath hub 24 therein. The pocket 81 and the balloon 72 are joined to each other by fusion-bonding (with heating, high-frequency radiation, ultrasonic radiation, etc.) or adhesion (with adhesive or solvent). The pocket 81 shown in FIG. 4 has at the right edge thereof the opening 83 for insertion into which the introducer sheath 25 is inserted and at the left edge thereof the outlet in the form of window opening 82. The sheath hub 24 tapers down toward its distal end. The introducer sheath 25 is inserted into the pocket 81 in such a way that the proximal end of the sheath hub 24 is disposed inside the pocket 81 and the root or proximal or trailing end portion of the sheath tube 23 extends out from the window 82. The window 82 has an inside diameter which is larger than the outside diameter of the leading end portion or tip of the sheath tube 23 and slightly smaller than the outside diameter of the trailing end portion or root of the sheath tube 23, so that the sheath tube 23 which has been inserted into the pocket 81 is not unexpectedly displaced. When the introducer sheath 25 is inserted into the blood vessel, the sheath tube 23 is introduced into the blood vessel until its root reaches the blood vessel. After this procedure is complete and the sheath tube 23 is withdrawn, the incision 201 in which the sheath tube 23 was inserted is the location where bleeding needs to be stopped. As mentioned above, the window 82 is arranged adjacent to the incision on the extension of the line connecting the position at which bleeding is to be stopped by the balloon 72 and the pocket 81. In addition, the balloon 72 presses the area surrounding the incision 201 including the area covering the adjacent window 82 of the pocket 81 and the root of the sheath tube 23 extending out therefrom. Therefore, it is possible to stop bleeding immediately by injecting a fluid into the balloon 72, without requiring that the hemostatic band 42 be rewound.

The position at which bleeding is to be stopped by the balloon 72 should preferably be located at the center of the balloon 72 or the intersection of the diagonals of the square forming the balloon 72. This makes it possible to align the center of the balloon 72 with the area of the incision 201, so that the balloon 72 securely applies its pressing force or pressure to the incision 201 and surrounding area when it is expanded.

The pocket 81 should preferably be formed from the same material as used for the band proper 71, balloon 72, and the auxiliary balloon 73, so that the pocket 81 and the balloon 72 are joined together easily or the band proper 71 and the balloons 72 and 73 are joined together easily by fusion bonding. This facilitates the production of the hemostatic band 42.

The pocket 81 and the balloon 72 are not specifically restricted in dimensions; the pocket 81 may have a length L1 of about 14 mm and the balloon 72 may have a length L2 of about 38 mm. In addition, that part of the sheath tube 23 which is inserted into the living body may be about 5 mm exposed from the pocket 81. These dimensions are adequate for the device which is downsized and integrally composed of the hemostatic band 42 and the introducer sheath 25, without impairing functioning of the hemostatic band 42.

Operation of the second embodiment will be explained below.

The procedure to insert the introducer sheath 25 into the artery in the wrist 200 is carried out in the same way as in the first embodiment. That is, the first step is to integrally fix the introducer sheath 25 and the dilator 31 together.

In the case where the introducer sheath 25 is previously received and held in the pocket 81 of the hemostatic band 42, the sheath tube 23 is introduced into the incision 201 and then the hemostatic band 42 is wound around the wrist 200 and the sheath hub 24. The hemostatic band 42 is fastened by means of the male part 51 and female part 52 of the hook-and-loop fastener 50 connected together while the hemostatic band 42 is wound around the wrist 200 and the sheath hub 24. This step may be changed in such a way that the hemostatic band 42 is wound around the wrist 200 and fixed or secured and then the sheath tube 23 is introduced into the incision 201 while the introducer sheath 25 is being held in the pocket 81. When this insertion step of the sheath tube 23 into the incision 201 completed, the sheath tube 23 and the dilator tube 32 stay disposed in the blood vessel and the sheath hub 24 and dilator hub 33 remain outside the patient's body.

Figure 5:
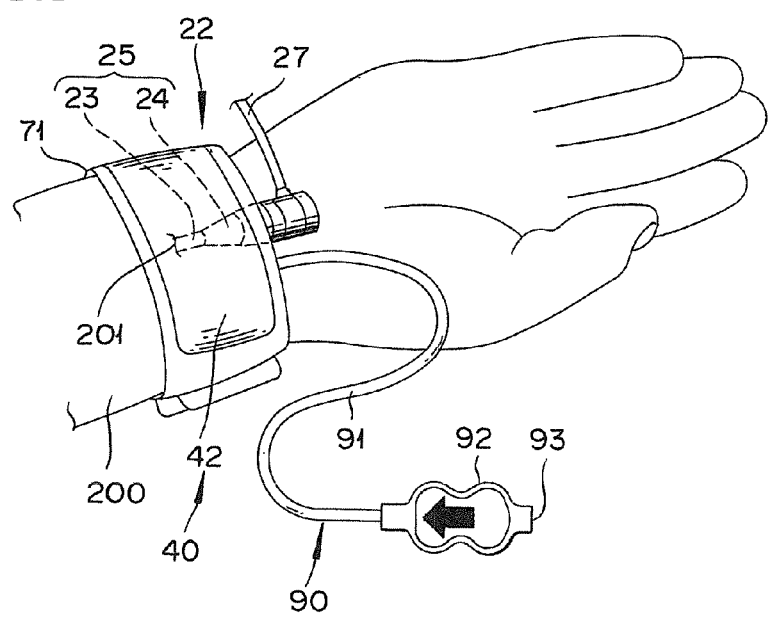
FIG. 5 is a diagram showing how the introducer sheath assembly pertaining to the second embodiment is mounted on the patient's wrist.

After the introducer sheath 25 has been inserted and the hemostatic band 42 has been secured or fastened about the patient's body, the dilator 31 is withdrawn, with the introducer sheath 25 remaining in place, as shown in FIG. 5. The sheath permits the catheter or the like to be inserted therethough and into the blood vessel.

During the course of the procedures described, the sheath hub 24 remains outside the patient's limb and the dilator hub 33 also remains outside the patient's body until the dilator 31 is withdrawn. Being fastened to the wrist 200 by the hemostatic band 42 wound around the wrist 200, the sheath hub 24 is less liable to be displaced and hence the sheath tube 23 is also less liable to be displaced.

The hemostatic band 42, which is entirely wound around the wrist 200, pushes the sheath hub 24 wholly against the wrist 200 with a strong fastening force thereby increasing the force fixing the sheath hub 24 in place.

Thus, as in the case of the first embodiment, the sheath tube 23, which has been inserted into the blood vessel, is securely fastened to such an extent that it will not be displaced even though the sheath hub 24 or the dilator hub 33 is touched or accidentally engaged by the operator. This facilitates the accurate and precise manipulation of the catheter and guide wire. Moreover, the fact that the hemostatic band 42 is connected to the sheath hub 24 through the pocket 81 also facilitates the step of attaching the introducer sheath 25 to the wrist 200.

Moreover, when the sheath tube 23 has been withdrawn after completion of the procedure, the incision 201 for the sheath tube 23 is the location of the patient's body where bleeding is to be stopped by the balloon 72, and the window 82 of the pocket 81 closely coincides with this location. Consequently, the injection of a fluid into the balloon 72 immediately stops bleeding without the necessity of rewinding the hemostatic band 42. This allows for a series of steps to be performed to stop bleeding after completion of the procedure that can be carried out simply and rapidly, without the possibility of blood leakage.

At the time bleeding is to be stopped, a syringe (not shown) is connected to the connector 93 of the injecting member 90 and a fluid is injected into the balloon 72 and the auxiliary balloon 73, so that the balloon 72 and the auxiliary balloon 73 are expanded. The degree of expansion of the balloon 72 and the auxiliary balloon 73 or the degree of pressing force onto the incision 201 can be easily adjusted by varying the amount of fluid for injection. After the balloon 72 and the auxiliary balloon 73 have been expanded, the syringe is detached from the connector 93 and then the introducer sheath 25 is withdrawn from the incision 201. According to an alternative procedure, it is possible to withdraw the introducer sheath 25 and then the fluid is injected into the balloon 72 and the auxiliary balloon 73. This procedure is desirable because the hemostatic band 42 has already been mounted to stop bleeding immediately.

As shown in FIG. 6, the balloon 72 and the auxiliary balloon 73 remain expanded and keep pressing the incision 201. In this state with the introducer sheath 25 withdrawn, the pocket 81 takes on its original shape or collapsed shape. As the balloon 72 locally presses the incision 201 (and the surrounding area of the patient's limb) and the balloon 72 and the auxiliary balloon 73 expand, the curved plate 74 separates from the surface of the wrist 200 and is made hard to touch the wrist 200. As the result, the incision 201 (and the neighborhood thereof) experiences a concentrated pressing force. This leads to a high hemostatic effect without pressing other blood vessels and nerves that do not need hemostasis. This is effective in preventing numbness and faulty circulation in the hand.

According to this embodiment, the hemostatic band 42 is constructed such that it can be freely and removably connected to the introducer sheath 25. Therefore, it can be suitably applied to the introducer sheath assembly 22, and it can also permit the introducer sheath assembly 22 to produce the aforementioned effect and the hemostatic band 42 to fully produce its inherent hemostatic function.

The ordinary hemostatic belt has a marker for alignment of the balloon with the incision. However, in the case of the introducer sheath assembly 22 according to the second embodiment does not need such a marker to assist the positioning of the balloon 72 because the introducer sheath 25 is integral with the hemostatic band 42 having the built-in balloon 72 and the balloon 72 presses the area including the window 82 of the pocket 81 and the root of the sheath tube 23.

Moreover, the holding part 80 is constructed of the pocket 81 having the window 82, and this structure permits the hemostatic band 42 to hold the introducer sheath 25 and also permits the hemostatic band 42 and the introducer sheath 25 to remain connected each other by the simple procedure of inserting the sheath tube 23 and the sheath hub 24 into the pocket 81.

According to the second embodiment, the hemostatic band 42 is provided with the pocket 81 having a simple bag-like structure which functions as the holding part 80 to hold the introducer sheath 25. However, the holding part 80 is not restricted to the one constructed as described above; it may be properly modified so long as it permits the hemostatic band 42 to hold the introducer sheath 25. An example of modification of the holding part 80 will be described below with reference to FIGS. 7(A) to 7(C), in which those elements common to the second embodiment are given identical symbols to partly avoid repeated descriptions.

Figure 7A:
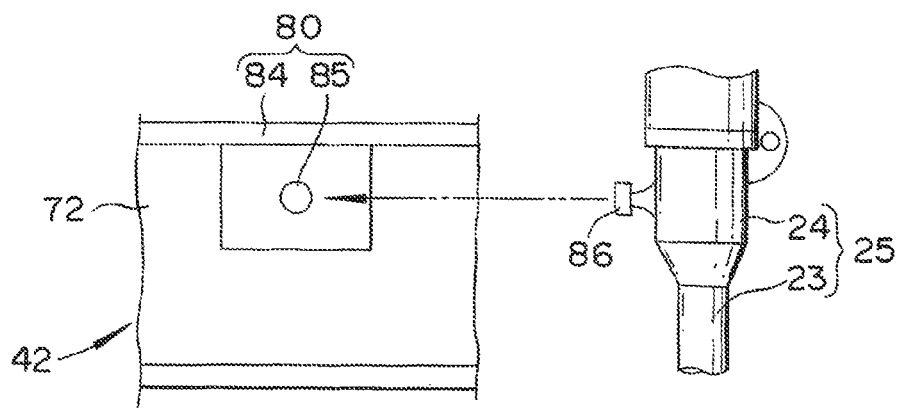
FIG. 7A is a plan view showing a modification of the holding part of the hemostatic band.

The holding part 80 may be constructed as shown in FIG. 7(A). In this form, the holding part 80 is composed of the supporting member 84 attached to the balloon 72 and the recess or aperture 85 which is formed in the supporting member 84 and capable of receiving the projection 86 fitted therethrough which is previously formed on the sheath hub 24. The projection 86 formed on the sheath hub 24 is fitted into the recess 85 formed in the supporting member 84. This simple step permits the hemostatic band 42 to hold the introducer sheath 25, so that the hemostatic band 42 and the introducer sheath 25 remain connected to each other.

The supporting member 84 may be made of the same material as the balloon 72 and the auxiliary balloon 73. The supporting member 84 is attached to the hemostatic band 42 by fusion bonding. The material for the supporting member 84 and the method for attaching the supporting member 84 to the hemostatic band 42 are not restricted to those described above and changes and modifications can be appropriately made.

The shape and position of the recess 85 are not specifically restricted, and the shape and position of the projections 86 are not specifically restricted. They may be appropriately changed and modified so long as they permit the hemostatic band 42 and the introducer sheath 25 to remain connected to each other. For example, the projection may be formed on the supporting member 84 and the recess may be formed in the introducer sheath 25.

Figure 7B:
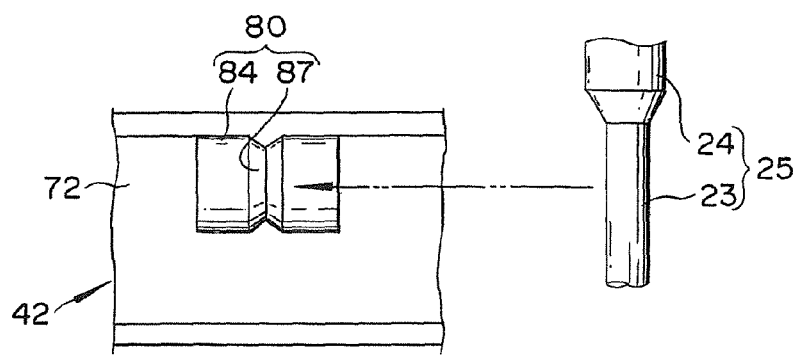
FIG. 7B is a plan view showing another modification of the holding part of the hemostatic band.

As shown in FIG. 7(B), the holding part 80 may be composed of the supporting member 84 attached to the balloon 72 and the slit-like groove 87 which is formed in the supporting member 84 and permits the sheath tube 23 to be inserted into the groove 87 formed in the supporting member 84. The sheath tube 23 is inserted into the groove 87 formed in the supporting member 84. This simple step permits the hemostatic band 42 to hold the introducer sheath 25, so that the hemostatic band 42 and the introducer sheath 25 remain connected to each other.

The supporting member 84 is made of flexible rubber material, and the width of the slit of the groove 87 is slightly narrower than the outside diameter of the sheath tube 23. Therefore, the sheath tube 23 can be easily inserted into the groove 87 by expanding the slit. After insertion, the sheath tube 23 is tightened with a comparatively weak force, so that the displacement of the sheath tube 23 is protected. Incidentally, the rubber material may be elastomer resin, and the supporting member 84 may be attached to the hemostatic band 42 by fusion bonding or adhesion.

The shape of the slit and position of the groove 87 are not specifically restricted but can be appropriately changed and modified so long as they permit the hemostatic band 42 and the introducer sheath 25 to remain connected to each other. A possible modification may be such that a part other than the sheath tube 23 of the introducer sheath 25 is inserted into the groove 87. In this case, the shape and position of the groove 87 may be appropriately changed according to the shape and position of the parts of the introducer sheath 25 to be inserted therein. The other part for insertion into the groove may be the sheath hub 24.

Figure 7C:
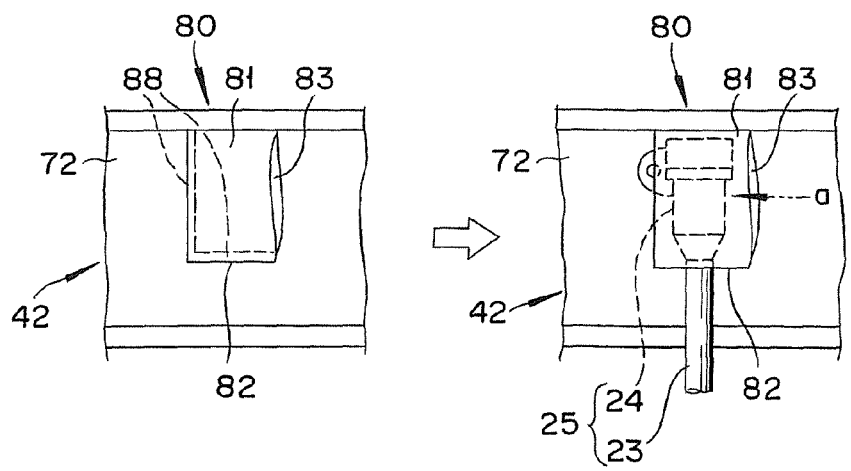
FIG. 7C is a plan view showing a further modification of the holding part of the hemostatic band.

The holding part 80 may be constructed of the pocket 81 having the holding hook-and-loop fastener 88, as shown in FIG. 7(C). The holding hook-and-loop fastener 88 is provided at the adjacent two sides of the pocket 81. One side (the left side in the figure) at which the holding hook-and-loop fastener 88 is provided may have the fastening part which holds a portion (say, suture eye) of the sheath hub 24 of the introducer sheath 25. The other side (the lower side in the figure) at which the holding hook-and-loop fastener 88 is provided has the part to hold and fasten the sheath tube 23. The other side further has the window 82 for the sheath tube 23 to pass through. That side on which the holding hook-and-loop fastener 88 is not provided has the insertion opening 83 through which the introducer sheath 25 is inserted into the pocket 81.

At the time of use, the sheath tube 23 and the sheath hub 24 are inserted into the pocket 81 through the insertion opening 83 (as indicated by the arrow a in the figure). The hemostatic band 42 is caused to hold the introducer sheath 25 by means of the holding hook-and-loop fastener 88. In this way the introducer sheath 25 is securely held without the possibility of displacement because the sheath hub 24 is fastened to one side of the pocket 81 and the sheath tube 23 is fastened to the other side of the pocket 81. The introducer sheath 25 is fastened simply by using the holding hook-and-loop fastener 88, and the hemostatic band 42 and the introducer sheath 25 remain connected to each other.

The pocket 81 is made of material identical or equivalent to that of the balloon 72 and the auxiliary balloon 73. The pocket 81 and the hemostatic band 42 are attached by fusion bonding. The material for the pocket 81 and the method for attaching the pocket 81 to the hemostatic band 42 are not restricted to those mentioned above; they may be changed and modified appropriately. The positions at which the pocket 81 and holding hook-and-loop fastener 88 are attached are not restricted either. They may be changed appropriately so long as they permit the hemostatic band 42 and the introducer sheath 25 to remain connected to each other.

The introducer sheath assemblies 21 and 22 and the hemostatic band 42 according to the present invention have been described above with reference to the illustrated embodiments. However, the scope of the present invention is not restricted to the particular embodiments described herein, and the constituents of the introducer sheath assemblies 21 and 22 and the hemostatic band 42 may be replaced by those capable of exhibiting the equivalent functions. Furthermore, any constituent parts may be added.

For example, the hook-and-loop fastener 50 provided on the belt member 41 as the belt 40 and the hemostatic band 42 may be replaced by any member which fastens the belt 40 and the sheath hub 24 which are wound around the wrist 200. Such exemplary members include a snap, button, clip, and frame (passing through the edge of the belt 40).

The foregoing describes an embodiment in which the marker to indicate the position for hemostasis is omitted. The embodiment may be modified such that a marker is attached to the balloon 72. If the balloon 72 is provided with a marker at the position corresponding to the incision 201 where the sheath tube 23 is inserted, the operator is able to clearly recognize the position for hemostasis.

The introducer sheath assemblies 21 and 22 and the hemostatic band 42 are not limited to be mounted on the wrist 200 and the introducer sheath assemblies 21 and 22 and the hemostatic band 42 may be mounted on the arm and leg (which are generally referred to as limbs in this specification).

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

The invention claimed is:

1. An introducer sheath assembly comprising:
    an introducer sheath having an elongate body for insertion into an incision in a patient's limb;
    an elongate securing device for being operatively connected to the elongate body to extend transversely thereto and being sized for extending about the patient's limb;
    a connector mechanism of the elongate securing device that is operable to releasably secure the elongate securing device about the patient's limb to urge a portion of the introducer sheath elongate body that remains outside the patient's body into tight engagement with the patient's limb;
    wherein the elongate securing device comprises a hemostatic band having a pressing device and a receiving portion configured to releasably receive and retain the elongate body portion of the introducer sheath with the pressing device generally aligned with the hemostatic band receiving portion and operable to exert pressure on an area of the patient's limb about the incision to stop bleeding from the incision after removal of the introducer sheath body therefrom;
    wherein the hemostatic band receiving portion has an outlet through which the elongate body extends for insertion into the incision adjacent thereto, and the pressing device comprises at least one inflatable member that is connected to the hemostatic band to overlap the hemostatic band receiving portion for exerting pressure on the area of the patient's limb about the incision; and
    wherein the hemostatic band receiving portion and the inflatable member are joined to each other by fusion-bonding or adhesion.

2. The introducer sheath assembly of claim 1 wherein the elongate securing device includes an elongate belt member, and the connector mechanism includes a hook-and-loop fastener having male and female portions thereof adjacent opposite ends of the elongate belt member that allow the elongate belt member to be tightly secured about the patient's limb to exert a downward pulling force on either side of the introducer sheath elongate body portion.

3. The introducer sheath assembly of claim 1 wherein the elongate securing device has one end directly connected to the elongate body of the introducer sheath.

4. The introducer sheath assembly of claim 3 wherein the elongate body of the introducer sheath includes a leading sheath tube portion for insertion into the incision and the portion of the elongate body that remains outside the patient's body comprises a trailing enlarged hub portion to which the one end of the elongate securing device is directly connected.

5. The introducer sheath assembly of claim 1 wherein the hemostatic band is of translucent or transparent material so that an operator can see therethrough to allow the receiving portion including the outlet thereof to be used as an indicator for properly securing the hemostatic band to the patient's limb so that the outlet is adjacent the incision and the pressing device is positioned to exert pressure on the area of the patient's limb about the incision.

6. The introducer sheath assembly of claim 1 wherein the hemostatic band includes a main elongate band portion having an outer surface for facing away from the patient's limb and an opposite inner surface for facing toward the patient's limb, the pressing device is secured to the inner surface of the main elongate band portion, and the hemostatic band receiving portion comprises a pocket fixed to the pressing device and having a window opening outlet through which the elongate body extends for insertion into the incision.

7. A hemostatic band device for an introducer sheath assembly having an introducer sheath including an elongate body having an enlarged, sheath hub portion and a tube portion for being inserted into an incision in a patient's limb, the hemostatic band device comprising:
   a hemostatic band for being operatively connected to the sheath elongate body to extend transversely thereto and being sized to extend about the patient's limb;
   at least one balloon of the hemostatic band that is expandable to apply pressure to an area of the patient's limb surrounding the incision;
   an introducer sheath receiving structure of the hemostatic band configured for removably receiving the sheath hub portion with the tube portion extending beyond the introducer sheath receiving structure to be inserted in the incision;
   wherein the introducer sheath receiving structure and the balloon are joined to each other by fusion-bonding or adhesion; and
   wherein the introducer sheath receiving structure comprises a pocket attached to the balloon, and the balloon is expanded before or after removal of the introducer sheath tube portion from the incision and the hub portion from the pocket to collapse the pocket attached thereto against the patient's limb adjacent to the incision after removal of the introducer sheath tube portion therefrom while applying pressure to the area of the patient's limb surrounding the incision.

8. The hemostatic band device of claim 7 wherein the pocket has an outlet window opening configured to tightly frictionally hold the tube portion extending out of the pocket through the outlet window opening.

9. The hemostatic band device of claim 7 in combination with the introducer sheath assembly wherein one of the pocket and the sheath hub portion has a projection and the other of the pocket and the sheath hub portion has an aperture sized to fit the projection extending therethrough for retaining the sheath hub portion in the pocket.

10. The hemostatic band device of claim 7 wherein the hemostatic band includes a main elongate band portion sized to extend about the patient's limb, and a connecting mechanism operable to releasably secure the main elongate band portion about the patient's limb and being disposed so that the connecting mechanism and the pocket including the balloon to which the pocket is attached are generally on opposite sides of the patient's limb.

11. A hemostatic band device for an introducer sheath assembly having an introducer sheath including an elongate body having an enlarged, sheath hub portion and a tube portion for being inserted into an incision in a patient's limb, the hemostatic band device comprising:
   a hemostatic band for being operatively connected to the sheath elongate body to extend transversely thereto and being sized to extend about the patient's limb;
   at least one balloon of the hemostatic band that is expandable to apply pressure to an area of the patient's limb surrounding the incision;
   an introducer sheath receiving structure of the hemostatic band configured for removably receiving the sheath hub portion with the tube portion extending beyond the introducer sheath receiving structure to be inserted in the incision;
   wherein the introducer sheath receiving structure comprises a pocket attached to the balloon, and the balloon is expanded before or after removal of the introducer sheath tube portion from the incision and the hub portion from the pocket to collapse the pocket attached thereto against the patient's limb adjacent to the incision after removal of the introducer sheath tube portion therefrom while applying pressure to the area of the patient's limb surrounding the incision;
   wherein the pocket has an outlet window opening configured to tightly frictionally hold the tube portion extending out of the pocket through the outlet window opening; and
   wherein the pocket includes a hook-and-loop fastener extending about the outlet window opening thereof for closing the outlet window opening tightly about the tube portion extending therethrough.

12. A hemostatic band device in combination with an introducer sheath assembly having an introducer sheath including an elongate body having an enlarged, sheath hub portion and a tube portion for being inserted into an incision in a patient's limb, the combination comprising:
   a hemostatic band for being operatively connected to the sheath elongate body to extend transversely thereto and being sized to extend about the patient's limb;
   at least one balloon of the hemostatic band that is expandable to apply pressure to an area of the patient's limb surrounding the incision;
   an introducer sheath receiving structure of the hemostatic band configured for removably receiving the sheath hub portion with the tube portion extending beyond the introducer sheath receiving structure to be inserted in the incision;
   wherein the introducer sheath receiving structure comprises a pocket attached to the balloon, and the balloon is expanded before or after removal of the introducer sheath tube portion from the incision and the hub portion from the pocket to collapse the pocket attached thereto against the patient's limb adjacent to the incision after removal of the introducer sheath tube portion therefrom while applying pressure to the area of the patient's limb surrounding the incision;
   wherein the pocket has an outlet window opening configured to tightly frictionally hold the tube portion extending out of the pocket through the outlet window opening; and
   wherein the introducer sheath tube portion has a smaller diameter, leading end portion and a larger diameter, trailing end portion adjacent the hub portion, and the pocket outlet window opening is sized in clearance with the leading end portion and in interference with the trailing end portion to allow the tube portion to be tightly frictionally held as the tube portion extends out of the pocket through the outlet window opening.

* * * * *